(12) United States Patent
Umakoshi et al.

(10) Patent No.: US 8,124,784 B2
(45) Date of Patent: Feb. 28, 2012

(54) PALLADIUM METAL COMPLEX

(75) Inventors: Keisuke Umakoshi, Nagasaki (JP);
Kazutoyo Kimura, Nagasaki (JP);
Masayoshi Onishi, Nagasaki (JP); Shoji Ishizaka, Sapporo (JP); Noboru Kitamura, Sapporo (JP); Satoshi Mikami, Takarazuka (JP)

(73) Assignees: Nagasaki University, Nagasaki (JP);
Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/867,188

(22) PCT Filed: Feb. 12, 2009

(86) PCT No.: PCT/JP2009/052288
§ 371 (c)(1),
(2), (4) Date: Aug. 11, 2010

(87) PCT Pub. No.: WO2009/101966
PCT Pub. Date: Aug. 20, 2009

(65) Prior Publication Data
US 2010/0311982 A1    Dec. 9, 2010

(30) Foreign Application Priority Data
Feb. 15, 2008   (JP) .................... 2008-034306

(51) Int. Cl.
*C07F 19/00* (2006.01)
(52) U.S. Cl. ...................................... 548/103
(58) Field of Classification Search ............ 548/103
See application file for complete search history.

(56) References Cited

U.S. PATENT DOCUMENTS
2009/0167157 A1   7/2009   Murakami et al.
(Continued)

FOREIGN PATENT DOCUMENTS
JP   2006-028101 A   2/2006

OTHER PUBLICATIONS

Keisuke Umakoshi et al., "Heteropolynuclear Palladium Complexes with Pyrazolate and its 3-*tert*-Butyl Derivatives: The Effect of Heterometal Ions on the Rate of Isomerization", Chemistry A European Journal, 2006, pp. 5094-5104, vol. 12, No. 19.

(Continued)

*Primary Examiner* — Rebecca Anderson
*Assistant Examiner* — Samantha Shterengarts
(74) *Attorney, Agent, or Firm* — Sughrue Mion, PLLC

(57) ABSTRACT

Disclosed is a metal complex containing a composition represented by the following formula (a). $[(Pd^{II})_2(M^I)_2(X)_2(L)_4(L')_2]$ (In the formula (a), $M^I$ represents $Ag^I$, $Au^I$ or $Cu^I$; X represents Cl, Br or I; L represents a group represented by formula (1); L' represents a group represented by formula (2); two $M^I$s may be the same as or different from each other; four Ls may be the same as or different from each other; and two L's may be the same as or different from each other.) (In the formulae (1) and (2), $R^1$, $R^2$ and $R^3$ independently represent a hydrogen atom, a halogen atom, a hydroxy group, an optionally substituted alkyl group, an optionally substituted aryl group or an optionally substituted monovalent heterocyclic group.)

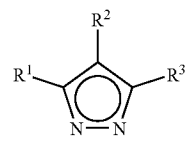

(1)

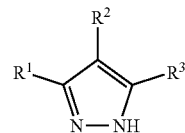

(2)

7 Claims, 1 Drawing Sheet

U.S. PATENT DOCUMENTS

2009/0198069 A1    8/2009    Umakoshi et al.

OTHER PUBLICATIONS

Keisuke Umakoshi et al., "Pyrazolato-Bridged Polynuclear Palladium and Platinum Complexes. Synthesis, Structure, and Reactivity.", Inorganic Chemistry, 2003, pp. 3907-3916, vol. 42, No. 12.

Juan Fornies et al., "Polynuclear Palladium Complexes with 3,5-Dimethylpyrazolate Exhibiting Three Different Coordination Modes", Chemical A European Journal, 2003, pp. 3427-3435, vol. 9, No. 14.

G. Attilio Ardizzoia et al., Polynuclear pyrazolato complexes. Synthesis, chemical reactivity and crystal structures of [{Pd(dmpz)$_2$(Hdmpz)$_2$}$_2$] and [{PdAg$_2$(dmpz)$_4$}$_2$] (Hdmpz = 3,5-dimethypyrazole), Journal of Chemical Society, Dalton Transactions, 1996, pp. 1351-1357, vol. 7.

Frederic W. Swamer et al. "Claisen Acylations and Carbethoxylations of Ketones and Esthers by Means of Sodium Hydride", Journal of the American Chemical Society, Mar. 1950, pp. 1352-1356, vol. 72, No. 3.

Mm. G. Bertrand et al., Bulletin de la Societe Chimique de France, (1929), pp. 877-884.

Chem. Abstr., 24, 1930, p. 7541.

A. Gonzalez et al., "Metal Complexes in Organic Synthesis.", Tetrahedron, 1986, pp. 4253-4257, vol. 42, No. 15.

Chiara B. Vicentini et al., "Chemoselective Synthesis of 3- and 5-Pyrazolylacetates", Heterocycles, 2000, pp. 1285-1292, vol. 53, No. 6.

Enzo Sottofattori et al.,"Synthesis of New Heterocyclic Derivatives of Retinoids", Journal of Heterocyclic Chemistry, Nov.-Dec. 1998, vol. 35, No. 6.

55th JSCC Symposium Abstract, p. 16, 11E-19 (2005) with translation.

55th JSCC Symposium Abstract, p. 354, PE-015 (2005) with translation.

56th JSCC Symposium Abstract, p. 195, 1PB114 (2006) with translation.

56th JSCC Symposium Abstract, p. 366, 2PE235 (2006) with translation.

56th JSCC Symposium Abstract, p. 366, 2PE236 (2006) with translation.

Office Action issued Sep. 30, 2011, in corresponding Chinese Patent Application No. 200980104920.5 with English translation.

PALLADIUM METAL COMPLEX

CROSS REFERENCE TO RELATED APPLICATIONS

This application is a National Stage of International Application No. PCT/JP2009/052288 filed Feb. 12, 2009, claiming priority based on Japanese Patent Application No. 2008-034306 filed Feb. 15, 2008, the contents of all of which are incorporated herein by reference in their entirety.

TECHNICAL FIELD

The present invention relates to a palladium mixed-metal complex.

BACKGROUND ART

Palladium mixed-metal complexes have been actively developed because they are useful as materials of organic electroluminescent light-emitting devices and the like.

A polynuclear complex [Pd$_2$Ag$_4$(μ-dmpz)$_8$] in which 3,5-dimethylpyrazolate (hereinafter referred to as "dmpz"), a monovalent anion formed by the dissociation of one proton from 3,5-dimethylpyrazole (dmpzH), bridges two Pd$^{II}$ ions and four Ag$^I$ ions is proposed as a palladium mixed-metal complex (NON-PATENT DOCUMENT 1).
NON-PATENT DOCUMENT 1: G A. Ardizzoia, G La Monica, S. Cenini, M. Moret, N. Masciocchi, J. Chem. Soc., Dalton Trans. 1996, 1351-1357.

DISCLOSURE OF THE INVENTION

Problems to be Solved by the Invention

However, a wide variety of palladium mixed-metal complexes exhibiting more excellent light emission properties are required. Accordingly, it is an object of the present invention to provide a new palladium mixed-metal complex that can be used as the light-emitting material of an organic electroluminescent device and the like and exhibits excellent light emission properties.

Means for Solving the Problems

First, the present invention provides a metal complex comprising a composition represented by the following formula (a):

[(Pd$^{II}$)$_2$(M$^I$)$_2$(X)$_2$(L)$_4$(L')$_2$]  (a)

wherein M$^I$ represents Ag$^I$, Au$^I$, or Cu$^I$; X represents Cl, Br, or I; L is represented by the following formula (1); and L' is represented by the following formula (2). Where two M$^I$s may be the same or different, four Ls may be the same or different, and two L's may be the same or different.
The formulas (1) and (2) are given by:

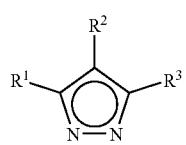
(1)

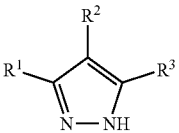
(2)

wherein R$^1$, R$^2$, and R$^3$ each independently represent a hydrogen atom, a halogen atom, a hydroxy group, an alkyl group which may be substituted, an aryl group which may be substituted, or a monovalent heterocyclic group which may be substituted.

Secondly, the present invention provides a light-emitting device comprising a light-emitting layer comprising the metal complex.

Thirdly, the present invention provides a display comprising the light-emitting device.

ADVANTAGE OF THE INVENTION

The metal complex of the present invention exhibits excellent light emission properties and is a new metal complex. Further, the metal complex of the present invention is particularly useful for a light-emitting device, a light-emitting apparatus, and the like, and a light-emitting device and a light-emitting apparatus using this metal complex also have excellent light emission properties.

BEST MODE FOR CARRYING OUT THE INVENTION

Figure 1:
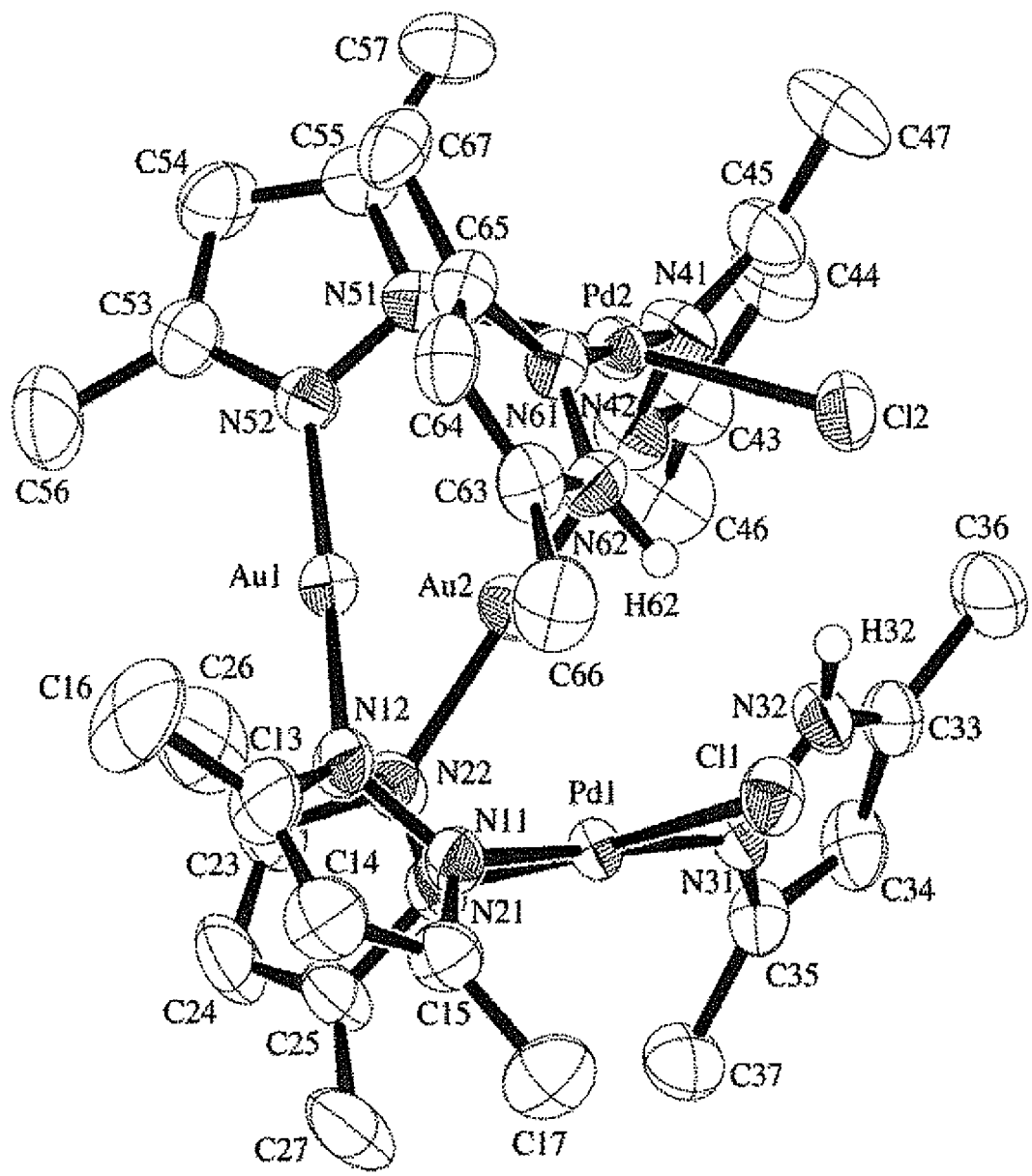
FIG. 1 is an ORTEP diagram showing the molecular structure of a metal complex A.

The best mode for carrying out the present invention will be described below.
<Metal Complex>
The metal complex of the present invention is a metal complex comprising the composition represented by the above formula (a).
In the above formula (a), M$^I$ represents Ag$^I$, Au$^I$, or Cu$^I$, and is preferably Au$^I$.
In the above formula (a), X represents Cl, Br, or I, and is preferably Cl.
In the above formula (a), L is represented by the above formula (1), and L' is represented by the above formula (2).
In the above formulas (1) and (2), R$^1$, R$^2$, and R$^3$ each independently represent a hydrogen atom, a halogen atom, a hydroxy group, an alkyl group which may be substituted, an aryl group which may be substituted, or a monovalent heterocyclic group which may be substituted. Preferably, at least one of R$^1$, R$^2$, and R$^3$ is a halogen atom, a hydroxy group, an alkyl group which may be substituted, an aryl group which may be substituted, or a monovalent heterocyclic group which may be substituted (that is, at least one of R$^1$, R$^2$, and R$^3$ is not a hydrogen atom). More preferably, at least one of R$^1$, R$^2$, and R$^3$ is an alkyl group which may be substituted, or an aryl group which may be substituted.

Examples of the above halogen atom include a fluorine atom, a chlorine atom, a bromine atom, and an iodine atom. The above halogen atom is preferably a chlorine atom.

The above alkyl group which may be substituted usually has about 1 to 6 carbon atoms, preferably 1 to 4 carbon atoms. Examples of the above alkyl group which may be substituted include unsubstituted alkyl groups, such as a methyl group, an ethyl group, a propyl group, an isopropyl group, a butyl group, an isobutyl group, a t-butyl group, a pentyl group, a hexyl group, and a cyclohexyl group; and substituted alkyl groups (particularly, alkyl groups substituted with a halogen atom, such as a fluorine atom), such as a trifluoromethyl group, a pentafluoroethyl group, a perfluorobutyl group, a perfluorohexyl group, and a perfluorooctyl group. A methyl group, an ethyl group, a t-butyl group, and a trifluoromethyl group are preferred.

The above aryl group which may be substituted is an atomic group formed by removing one hydrogen atom from an aromatic hydrocarbon which may be substituted. Here, the above aromatic hydrocarbon includes those having a condensed ring, and those in which two or more independent benzene rings or condensed rings are bonded directly or via a group, such as vinylene. The above aryl group which may be substituted usually has about 6 to 20 carbon atoms, preferably 6 to 10 carbon atoms. Examples of the above aryl group which may be substituted include unsubstituted aryl groups, such as a phenyl group, a $C_1$ to $C_4$ alkoxyphenyl group ("$C_1$ to $C_4$ alkoxy" indicates that the alkoxy portion has 1 to 4 carbon atoms. The same applies hereinafter.), a $C_1$ to $C_4$ alkylphenyl group ("$C_1$ to $C_4$ alkyl" indicates that the alkyl portion has 1 to 4 carbon atoms. The same applies hereinafter.), a 1-naphthyl group, and a 2-naphthyl group; and substituted aryl groups (particularly, aryl groups substituted with a halogen atom, such as a fluorine atom), such as a pentafluorophenyl group. A phenyl group, a methylphenyl group, and a t-butylphenyl group are preferred.

The above monovalent heterocyclic group which may be substituted means a group formed by removing one atom or group from a heterocyclic compound in which elements constituting a ring are not limited to a carbon atom and which contains a nitrogen atom, an oxygen atom, a sulfur atom, and the like as a heteroatom in the ring. A monovalent aromatic heterocyclic group which may be substituted is preferred as the above monovalent heterocyclic group which may be substituted.

Examples of the above L represented by the above formula (1) include pyrazolate (a monovalent anion formed by the dissociation of a hydrogen ion from a pyrazole compound). Specific examples of the above formula (1) include the following:

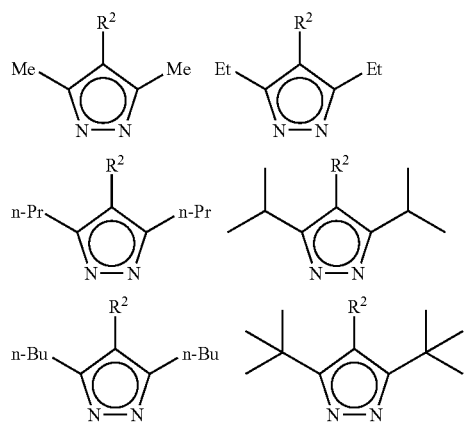

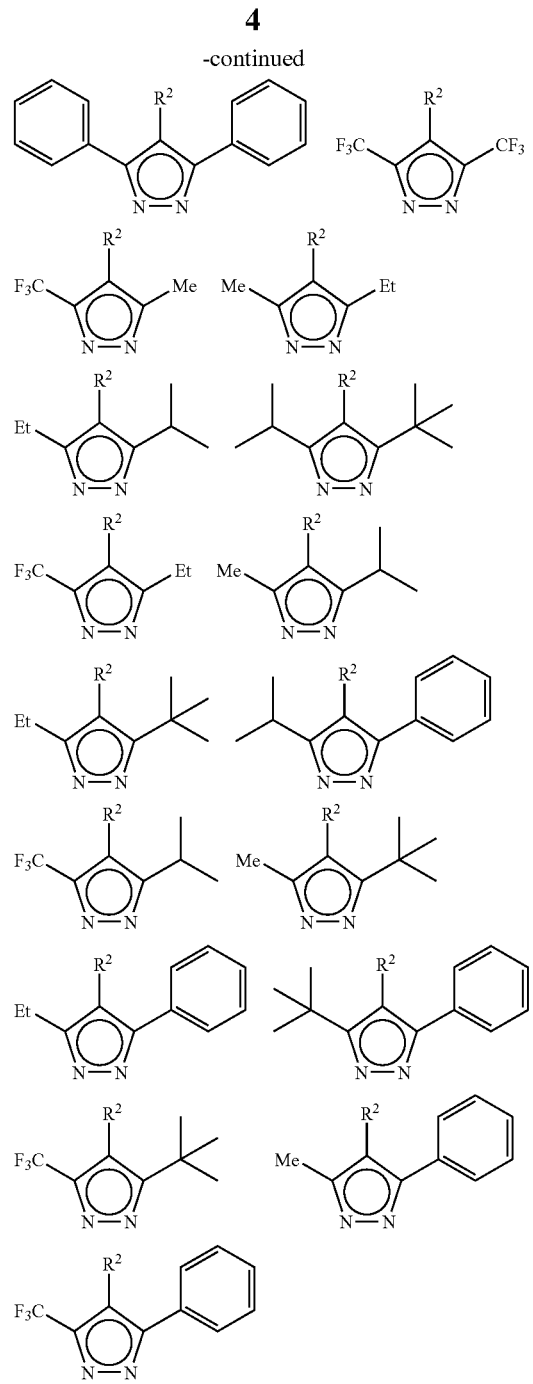

wherein $R^2$ has the same meaning as described above, Me represents a methyl group, Et represents an ethyl group, n-Pr represents an n-propyl group, and n-Bu represents an n-butyl group.

Examples of L' represented by the above formula (2) include the following:

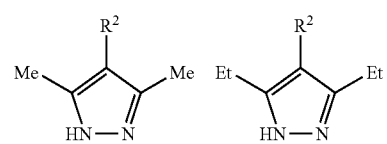

-continued

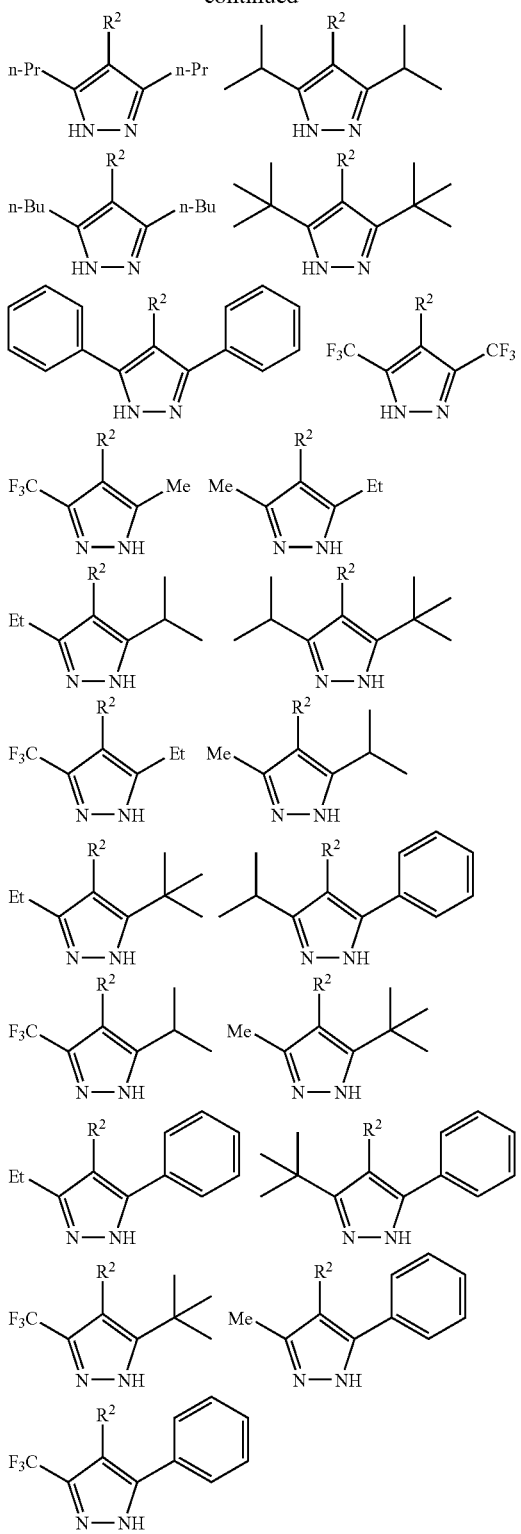

wherein R² has the same meaning as described above, Me represents a methyl group, Et represents an ethyl group, n-Pr represents an n-propyl group, and n-Bu represents an n-butyl group.

R¹, R², and R³ in the above formulas (1) and (2) may be the same or different in each of L and L'.

The above L' may be synthesized by any method. For example, a pyrazole compound (B) can be synthesized by obtaining a diketone compound (A) as an intermediate by the method described in J. Am. Chem. Soc., 72, 1352-1356 (1950), and reacting the diketone compound (A) with hydrazine or hydrazine monohydrate by the methods described in Bull. Soc. Chim., 45, 877-884 (1929), Chem. Abstr., 24, 7541 (1930), Tetrahedron, 42, 15, 4253-4257 (1986), and Heterocycles, 53, 1285 (2000) (the following Scheme 1). The above diketone compound (A) may be synthesized, for example, by the oxidation reaction of a β-unsaturated ketone, or the reaction of a ketocarboxylic acid with a Grignard reagent from alkyl bromide. The above L' may also be synthesized by the method described in J. Heterocyclic Chem., 35, 1377 (1998).

[Scheme 1]

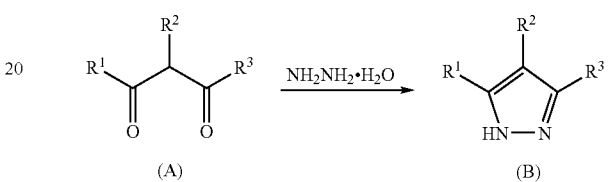

The metal complex of the present invention is preferably a metal complex comprising a composition represented by the following formula (b) as the composition represented by the above formula (a):

$$[\{(Pd^{II})(M^{I})(X)(L)_2(L')\}_2] \quad (b)$$

wherein $M^I$, X, L, and L' represent the same meanings as described above.

The metal complex comprising the composition represented by the above formula (b) can be regarded as one in which two $\{(Pd^{II})(M^{I})(X)(L)_2(L')\}$ units are dimerized, comprises a metal complex in which L bridges $Pd^{II}$ and $M^I$ and the metal atoms interact with each other in the ground state or the excited state, and has, for example, a structure represented by the following formula (3) or (4):

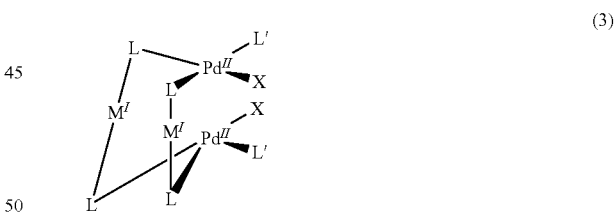

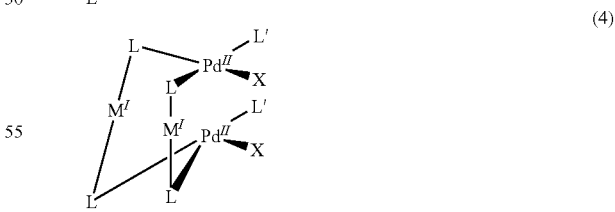

wherein $M^I$, X, L, and L' represent the same meanings as described above.

For the metal complex of the present invention, a case where a two-fold rotation axis passing through the midpoint of a line segment connecting two $Pd^{II}$s and the midpoint of a line segment connecting two $M^I$s is present in the molecule (in this case, R¹ and R³ in the above L are the same) and a case where the two-fold rotation axis is not present (in this case, R¹ and $R^3$ in the above L are different) are possible. In terms of the ease of the acquisition, synthesis, and purification of compounds which are ligands, the case where the two-fold rotation axis is present is preferred. When the above two-fold rotation axis is not present, various geometrical isomers having different L and L' can be present, and the geometrical isomers have different light emission energy levels. For example, the above two-fold rotation axis can be present in the structure represented by the above formula (3), and the above two-fold rotation axis is not present in the structure represented by the above formula (4).

The metal complex of the present invention may be synthesized by any method. For example, a metal complex comprising a composition represented by the formula: $[Pd_2Au_2Cl_2(\mu\text{-dmpz})_4(dmpzH)_2]$ can be synthesized by reacting $[PdCl_2(CH_3CN)_2]$, dmpzH, and $AuCl(SC_4H_8)$ in the presence of triethylamine. Here, $[Pd_2Au_2Cl_2(\mu\text{-dmpz})_4(dmpzH)_2]$ is a metal complex in which part of dmpzH ligands are not deprotonated and are coordinated in an uncharged state. $[Pd_2Au_2Br_2(\mu\text{-dmpz})_4(dmpzH)_2]$ and $[Pd_2Au_2I_2(\mu\text{-dmpz})_4(dmpzH)_2]$ can also be similarly synthesized. "dmpzH" represents 3,5-dimethylpyrazole, and "dmpz" represents 3,5-dimethylpyrazolate (a monovalent anion formed by the dissociation of a hydrogen ion from 3,5-dimethylpyrazole).

The metal complex of the present invention is particularly useful as a light-emitting material contained in the light-emitting layer of a light-emitting device, such as an organic electroluminescent device, and is also useful for sensors for organic molecules, gas molecules, and the like, antitumor agents, paints that are usually colorless and transparent but emit light only during ultraviolet light irradiation, and the like.

Next, a light-emitting device having a light-emitting layer comprising a metal complex according to the present invention will be described.

The light-emitting device of the present invention is not particularly limited as long as it has a light-emitting layer comprising the above metal complex. For example, the light-emitting device of the present invention is a light-emitting device in which an anode, a hole injection layer, a hole transport layer, a light-emitting layer, an electron transport layer, an electron injection layer, and a cathode are formed in this order on a transparent substrate. Furthermore, the light-emitting device of the present invention is not limited to this five-layer light-emitting device and may be a four-layer light-emitting device in which the electron transport layer is omitted from the five-layer light-emitting device, a three-layer light-emitting device in which the hole injection layer and the electron injection layer are omitted from the five-layer light-emitting device, a two-layer light-emitting device in which the light-emitting layer and electron transport layer of the three-layer light-emitting device are used as one layer in combination, or a single-layer light-emitting device in which only a light-emitting layer is formed between an anode and a cathode. This metal complex can be used for both the single-layer light-emitting device and the multilayer light-emitting device. But, when the metal complex is used for the single-layer light-emitting device, it tends to be easy to obtain more excellent light emission properties.

A light-emitting device to which the above metal complex can be advantageously applied is a light-emitting device comprising the above metal complex in a light-emitting layer and is usually a multilayer light-emitting device comprising an anode to which positive voltage is applied, a cathode to which negative voltage is applied, a hole injection layer and a hole transport layer for injecting holes from the anode and transporting the holes, an electron injection layer and an electron transport layer for injecting electrons from the cathode and transporting the electrons, and a light-emitting layer for recombining holes and electrons and providing light emission. The above metal complex is useful as a host light-emitting material in the light-emitting device. Further, the above metal complex can also be used as materials of the hole injection layer, the hole transport layer, the electron injection layer, the electron transport layer, and the like. Further, other host light-emitting materials, including metal complexes containing 8-quinolinols as ligands, such as tris(8-hydroxyquinolinato)aluminum, also function as guest light-emitting materials for improving the light emission efficiency and emission spectrum, by doping in a slight amount. Therefore, other than being used alone, the metal complex of the present invention can also be used as a composition in combination with, for example, other light-emitting materials, such as dicyanomethylenes (DCMs), coumarins, perylenes, and rubrenes, and the materials of the hole injection layer, the hole transport layer, the electron injection layer, the electron transport layer, and the like.

The light-emitting device of the present invention can be used in a display. In other words, the display of the present invention is a display comprising the above light-emitting device.

EXAMPLE

Next, an Example(s) according to the present invention will be described. However, the present invention is not limited to these Examples.

Example 1

Synthesis of $[Pd_2Au_2Cl_2(\mu\text{-dmpz})_4(dmpzH)_2]$

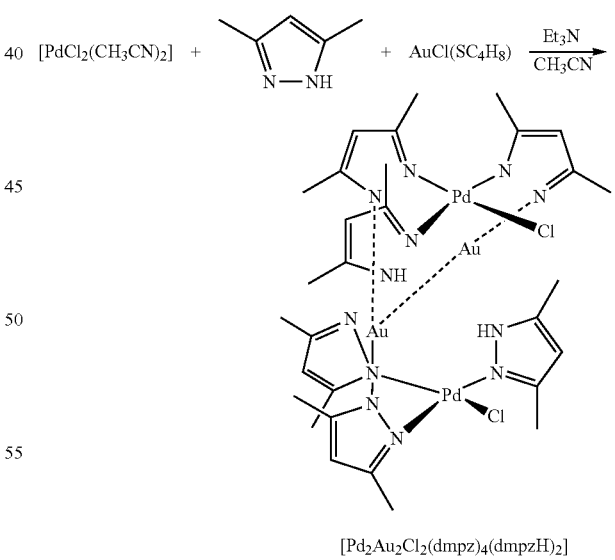

$[Pd_2Au_2Cl_2(dmpz)_4(dmpzH)_2]$

An acetonitrile solution (5 ml) of $AuCl(SC_4H_8)$ (64 mg, 0.20 mmol), an acetonitrile solution (5 ml) of 3,5-dimethylpyrazole (58 mg, 0.6 mmol), and triethylamine (85 µl, 0.6 mmol) were added, with stirring, to an acetonitrile solution (5 ml) of $[PdCl_2(CH_3CN)_2]$ (52 mg, 0.20 mmol) under an argon atmosphere, and they were stirred under the argon atmosphere at room temperature for 3.5 hours. The solution which was yellow at first changed gradually to a yellow suspension. This suspension was filtered, and the obtained filtrate was evaporated slowly under air. 12 mg of a yellow crystalline compound (hereinafter referred to as a "metal complex A") was obtained (yield: 9.3%).

This metal complex A was identified by an IR spectrum, elementary analysis, $^1$H NMR, and FAB-MS, and found to be [Pd$_2$Au$_2$Cl$_2$(μ-dmpz)$_4$(dmpzH)$_2$]. IR (KBr): 3224 (br), 3145 (w), 3047 (w), 2975 (m), 2921 (s), 2361 (w), 2341 (w), 2251 (w), 1577 (s), 1534 (s), 1480 (m), 1416 (s), 1378 (m), 1353 (s), 1279 (m), 1174 (m), 1055 (m), 980 (w), 815 (m), 787 (s), 764 (s), 679 (m), 653 (m), 594 (m), 479 (w), 470 (w), 446 (w)

Elementary analysis: Calculated values for C$_{32}$H$_{47}$Au$_2$Cl$_2$N$_{13}$Pd$_2$ (calculated in a form containing one molecule of acetonitrile as the crystal solvent, that is, [Pd$_2$Au$_2$Cl$_2$(μ-dmpz)$_4$(dmpzH)$_2$]·CH$_3$CN): C 29.76; H 3.67; N 14.10%. Measured values: C 29.93; H 3.59; N 14.37%.

TABLE 1

$^1$H NMR Data of [Pd$_2$Au$_2$Cl$_2$(μ-dmpz)$_4$(dmpzH)$_2$](CDCl$_3$, TMS, 300 MHz)

| δ (ppm) | Form of signal | Intensity | Assignment |
|---|---|---|---|
| 12.01 | s | 1 | NH |
| 5.81 | s | 1 | H4 |
| 5.76 | s | 1 | H4 |
| 5.57 | d | 1 | H4 |
| 2.75 | s | 3 | CH$_3$ |
| 2.17 | s | 3 | CH$_3$ |
| 2.11 | s | 3 | CH$_3$ |
| 1.89 | s | 3 | CH$_3$ |
| 1.72 | s | 3 | CH$_3$ |
| 1.65 | s | 3 | CH$_3$ |

Mass analysis was also performed by the FAB-MS method for the metal complex A. The obtained result was as follows.

FAB-MS: m/z: 1251.1 [M+H]$^+$ (wherein M represents the complex molecule [Pd$_2$Au$_2$Cl$_2$(μ-dmpz)$_4$(dmpzH)$_2$])

The solubility of the metal complex A in organic solvents was tested. The metal complex A was soluble in chloroform and methylene chloride, slightly soluble in toluene and benzene, and insoluble in ethanol, acetone, diethyl ether, methanol, acetonitrile, and hexane.

The structure of the metal complex A will be described. [Pd$_2$Au$_2$Cl$_2$(μ-dmpz)$_4$(dmpzH)$_2$] crystallized in a form containing one molecule of acetonitrile. The molecular structure was determined by single crystal X-ray structure analysis. Its crystallographic data is shown in Table 2.

TABLE 2

Crystallographic Data of [Pd$_2$Au$_2$Cl$_2$(μ-dmpz)$_4$(dmpzH)$_2$]·CH$_3$CN

| | [Pd$_2$Au$_2$Cl$_2$(μ-dmpz)$_4$(dmpzH)$_2$]·CH$_3$CN |
|---|---|
| Empirical formula | C$_{32}$H$_{47}$Au$_2$Cl$_2$N$_{13}$Pd$_2$ |
| Formula weight | 1291.45 |
| Measurement temperature (K) | 296 |
| X-ray wavelength (Å) | 0.71070 (MoKα ray) |
| Crystal system | Monoclinic system |
| Space group | P2$_1$/c (#14) |
| Lattice constant | |
| a(Å) | 11.5302 (4) |
| b(Å) | 16.4579 (5) |
| c(Å) | 22.4499 (7) |
| α(deg) | 90 |
| β(deg) | 90.5665 (4) |

TABLE 2-continued

Crystallographic Data of [Pd$_2$Au$_2$Cl$_2$(μ-dmpz)$_4$(dmpzH)$_2$]·CH$_3$CN

| | [Pd$_2$Au$_2$Cl$_2$(μ-dmpz)$_4$(dmpzH)$_2$]·CH$_3$CN |
|---|---|
| γ(deg) | 90 |
| Lattice volume (Å$^3$) | 4259.9 (2) |
| Z value | 4 |
| Density (calculated) (gm$^{-3}$) | 2.013 |
| Linear absorption coefficient μ(Mo Kα), cm$^{-1}$ | 78.87 |
| The number of independent reflections | 9677 (R$_{int}$ = 0.035) |
| The number of data and the number of parameters | 9677/0/460 |
| Final R value [I > 2σ(I)] | R1 = 0.029 |
| R value when total reflection is used | R = 0.048, Rw = 0.066 |
| GOF value | 0.92 |

An ORTEP diagram showing the molecular structure of the metal complex A ([Pd$_2$Au$_2$Cl$_2$(μ-dmpz)$_4$(dmpzH)$_2$]) is shown in FIG. 1. In FIG. 1, the element symbols H, Cl, Pd, and Au followed by numbers are given to represent atoms constituting the metal complex A. The metal complex A is a tetranuclear complex composed of two Pd$^{II}$ ions, two Au$^I$ ions, two chloride ions, four dmpz ligands, and two dmpzH ligands. Two dmpz ligands coordinating to each Pd atom bridge the Pd atom and the Au atoms, and one Cl atom and one dmpzH ligand respectively coordinate to the remaining coordination sites of each palladium (Pd) atom. Furthermore, each Cl atom forms a hydrogen bond with a dmpzH ligand coordinating to the other Pd atom. A pseudo two-fold rotation axis perpendicular to the Pd . . . Pd axis is present in the molecule. The Pd . . . Pd distance is 4.5330(5) Å, the Au . . . Au distance is 3.5319(3) Å, and the Pd . . . Au distances are in the range of 3.4144(4) to 3.5556(4) Å. Also, the Pd—Cl distances are 2.306(1) Å and 2.313(1) Å, the Pd—N distances are in the range of 1.995(4) to 2.027(4) Å, and the Au—N distances are in the range of 2.001(4) to 2.009(4) Å.

The metal complex A exhibited orange emission in the solid state by irradiation with ultraviolet light at 254 nm or 365 nm.

The invention claimed is:

1. A metal complex comprising a composition represented by the following formula (a):

[(Pd$^{II}$)$_2$(M$^I$)$_2$(X)$_2$(L)$_4$(L')$_2$]  (a)

wherein M$^I$ represents Ag$^I$, Au$^I$ or Cu$^I$; X represents Cl, Br, or I; L is represented by the following formula (1); and L' is represented by the following formula (2) where two M$^I$s may be the same or different, four Ls may be the same or different, and two L's may be the same or different, the formulas (1) and (2) being given by:

(1)

(2)

wherein $R^1$, $R^2$, and $R^3$ each independently represent a hydrogen atom, a halogen atom, a hydroxy group, an alkyl group which may be substituted, an aryl group which may be substituted, or a monovalent heterocyclic group which may be substituted.

2. The metal complex according to claim 1, comprising a composition represented by the following formula (b):

  (b)

wherein $M^I$, X, L, and L' represent the same meanings as described above.

3. The metal complex according to claim 1, wherein at least one of the $R^1$, $R^2$, and $R^3$ is a halogen atom, a hydroxy group, an alkyl group which may be substituted, an aryl group which may be substituted, or a monovalent heterocyclic group which may be substituted.

4. The metal complex according to claim 3, wherein at least one of the $R^1$, $R^2$, and $R^3$ is an alkyl group which may be substituted, or an aryl group which may be substituted.

5. The metal complex according to claim 1, wherein a two-fold rotation axis is present in a molecule thereof.

6. A light-emitting device comprising a light-emitting layer comprising the metal complex according to claim 1.

7. A display comprising the light-emitting device according to claim 6.

* * * * *